United States Patent
Bartels et al.

(10) Patent No.: US 11,793,947 B2
(45) Date of Patent: Oct. 24, 2023

(54) SEAL FOR AN INHALATION DEVICE

(71) Applicant: SOFTHALE NV, Diepenbeek (BE)

(72) Inventors: Frank Bartels, Hattingen (DE); Jürgen Rawert, Cologne (DE)

(73) Assignee: SOFTHALE NV, Diepenbeek (BE)

( * ) Notice: Subject to any disclaimer, the term of this patent is extended or adjusted under 35 U.S.C. 154(b) by 357 days.

(21) Appl. No.: 16/757,544

(22) PCT Filed: Oct. 17, 2018

(86) PCT No.: PCT/EP2018/078445
§ 371 (c)(1),
(2) Date: Apr. 20, 2020

(87) PCT Pub. No.: WO2019/076995
PCT Pub. Date: Apr. 25, 2019

(65) Prior Publication Data
US 2021/0196905 A1  Jul. 1, 2021

Related U.S. Application Data

(60) Provisional application No. 62/574,018, filed on Oct. 18, 2017.

(30) Foreign Application Priority Data

Oct. 18, 2017 (EP) .................................... 17197136

(51) Int. Cl.
*A61M 11/00* (2006.01)

(52) U.S. Cl.
CPC ... *A61M 11/007* (2014.02); *A61M 2205/0216* (2013.01); *A61M 2205/0222* (2013.01)

(58) Field of Classification Search
CPC ........ A61M 11/007; A61M 2205/0216; A61M 2205/0222; A61M 15/0065;
(Continued)

(56) References Cited

U.S. PATENT DOCUMENTS 3,471,065 A * 10/1969 Malone ................. B05B 9/0883
222/321.1
3,933,279 A * 1/1976 Maier ..................... F04B 29/00
222/631

(Continued)

FOREIGN PATENT DOCUMENTS

| CN | 104623772 A | 5/2015 |
|---|---|---|
| DE | 102005052898 A1 | 5/2007 |

(Continued)

OTHER PUBLICATIONS

"Dichtomatik O-Ring Handbook," *Dichtomatik North America*, XP055459547, pp. 21 and 132 (2006); http://www.allsealsinc.com/dichtomatik/dichtomatik_oring_handbook.pdf, retrieved on Mar. 15, 2018.

*Primary Examiner* — Colin W Stuart
*Assistant Examiner* — Matthew D Ziegler
(74) *Attorney, Agent, or Firm* — Pharma Patents International AG; Lily Ackerman

(57) ABSTRACT

The invention relates to the field of inhalation devices for liquids. In particular, the invention relates to an improved seal construction for an inhalation device having a nebulizing nozzle and a piston which moves relative to a pumping chamber in order to generate pumping pressure and to an inhalation device comprising such seal.

14 Claims, 9 Drawing Sheets

(58) Field of Classification Search
CPC ....... A61M 2205/8281; B05B 11/3091; B05B 11/305; B05B 1/265; B05B 11/00; B05B 11/0005; B05B 11/1012; B05B 11/1014; B05B 11/1001
USPC .................. 222/401, 321.9, 321.7, 383.1
See application file for complete search history.

(56) References Cited

U.S. PATENT DOCUMENTS

| | | | | |
|---|---|---|---|---|
| 5,370,317 | A * | 12/1994 | Weston | ................. B05B 11/007 239/533.13 |
| 6,789,702 | B2 * | 9/2004 | O'Connor | .............. B65D 83/66 222/335 |
| 8,550,300 | B2 * | 10/2013 | Lee | ..................... B05B 11/3074 222/105 |
| 9,050,428 | B2 * | 6/2015 | Dunne | .............. A61M 15/0065 |
| 9,192,734 | B2 * | 11/2015 | Hausmann | .......... B05B 11/3001 |
| 9,283,333 | B2 | 3/2016 | Schuy et al. | |
| 9,550,025 | B2 * | 1/2017 | Dunne | ................. A61M 5/3202 |
| 9,757,750 | B2 * | 9/2017 | Holakovsky | ........ B05B 11/0054 |
| 9,856,070 | B2 * | 1/2018 | Ghavami-Nasr | ...... B65D 83/48 |
| 2009/0166379 | A1 * | 7/2009 | Wright | .............. A61M 15/0028 604/58 |
| 2009/0236445 | A1 | 9/2009 | Lintern et al. | |
| 2017/0333922 | A1 * | 11/2017 | Selby | .................... A61M 11/00 |

FOREIGN PATENT DOCUMENTS

| | | |
|---|---|---|
| EP | 0 627 230 B1 | 2/2000 |
| WO | WO 2007/051536 | 5/2007 |
| WO | WO 2012/007315 A1 | 1/2012 |
| WO | WO 2016/075433 A1 | 5/2016 |
| WO | WO 2018/197730 A1 | 11/2018 |

* cited by examiner

SEAL FOR AN INHALATION DEVICE

CROSS-REFERENCE TO RELATED APPLICATIONS

This application is a United States Application under 35 U.S.C. § 371 claiming priority to and the benefit of PCT Application No. PCT/EP2018/078445, filed Oct. 17, 2018, which claims priority to and the benefit of European Application No. 17197136.9, filed on Oct. 18, 2017, and U.S. Provisional Application Ser. No. 62/574,018, filed on Oct. 18, 2017, the contents of each which are hereby incorporated by reference in their entirety.

FIELD OF THE INVENTION

The invention relates to the field of inhalation devices for liquids. In particular, the invention relates to an improved seal construction for an inhalation device having a nebulizing nozzle and a piston which moves relative to a pumping chamber in order to generate pumping pressure and to an inhalation device comprising such seal.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle. A pumping unit is defined as a unit or device component capable of moving or compressing a fluid material and that comprises at least one pumping chamber, and optionally further comprises auxiliary components as well, such as a body, interfaces, and the like. By means of the pumping unit, the liquid is drawn in a discrete amount, i.e. not continuously, from the reservoir, and fed to the nozzle. The pumping unit works without propellant and generates pressure mechanically.

This inhalation devices makes use of a fixed pumping chamber, into which a moveable and hollow piston can be inserted in order to decrease the interior volume of said chamber, thus increasing the pressure both in said chamber and the inside of the piston, eventually leading to atomization of the liquid from the nozzle. By again extracting the piston from the chamber, its interior volume is increased, and the resulting negative pressure leads to drawing liquid from the reservoir into the chamber, such that a new atomizing cycle can begin.

An improvement of such an inhalation device is disclosed in patent application EP 17168869, filed by the same applicant as the present invention. According to this improvement, the inhalation device provides a fixed piston and a moveable pumping chamber. By pushing the pumping chamber onto the hollow piston, the pressure is increased and the liquid is pressed out of the nozzle. By pulling the chamber from the piston, the pressure becomes negative and fresh liquid is drawn into the increasing volume of the chamber.

A common problem of both described constructions is the presence of a gap between the piston and the according bore in the pumping chamber. Due to the relative motion of these two components, a small gap is always present between the outside of the piston and the inner wall of the according bore hole. Although it is clear that the smaller the gap, the lower the loss of pressure becomes, the width of said gap cannot go below a certain value due to unavoidable variations of the respective walls. Therefore, a seal which is typically a ring shaped elastic seal is arranged in a circumferential groove that is placed on the inner wall of the pumping chamber, the seal touching the outside wall of the piston.

By repeatedly moving the piston relative to the pumping chamber, small particles can be abraded from the outside of the piston as well as from the seal surface region which slides along the outside wall of the piston. These particles can then migrate into the liquid, contaminating it. The particles can also result in clogging of the usually very fine nozzle channel(s).

In order to minimize the wear of the contacting surfaces, the quality of the outside wall of the piston must be high, resulting in high costs with respect to both the piston material and its processing.

In the co-pending patent application EP17168869.0, an alternative inhalation device is disclosed in which the pumping action is based on the relative motion between an immobile piston-like riser pipe and a moveable pumping chamber. In order to allow for such movement without a gap and a seal between the riser pipe and the pumping chamber, both the inner surface of the pumping chamber and the outer surface of the riser pipe would require a high degree of smoothness and resistance to wear. Such requirements are disadvantageous in terms of costs, and they are restrictive with respect to the materials that may be used.

OBJECT OF THE INVENTION

The object of the invention is the provision of a device that avoids one or more of the drawbacks of the known art.

For example, the problem of contamination of the liquid by abraded particles stemming from a sealing between piston and pumping chamber should be significantly reduced without increasing the cost of the device.

DESCRIPTION OF THE INVENTION

The object is solved by a device according to claim 1. In another aspect of the invention, the object is solved by a device according to claim 2. Advantageous embodiments are described in the dependent claims, the subsequent description, as well as the accompanying figures.

According to a first aspect of the invention, an inhalation device for medically active liquids for generation of an aerosol is provided which comprises a housing, an impingement-type nozzle for generating the nebulised aerosol by collision of at least two liquid jets, the nozzle being firmly affixed to the user-facing side of the housing such as to be immobile relative to the housing, inside the housing the inhalation device comprises a reservoir for storing a liquid, a pumping device with a pumping chamber for generation of a pressure inside said pumping chamber, wherein the pumping chamber is fluidically connected with the reservoir, optionally via a check valve which blocks in direction of the reservoir, a riser pipe which can be received with at least one reservoir-facing, interior end in said pumping chamber, and said nozzle which is connected liquid-tight to an exterior end of the riser pipe.

The nozzle used in the device according to the invention is of a type that is used in so-called soft mist inhalers, and configured to emit at least two jets of liquid to be nebulized such as to collide and form an aerosol of dispersed liquid droplets in air. Such nozzles are adapted to function at relatively high pressure, such as in the range from about 10 bar to about 100 bar.

As such, the inhalation device is adapted to operate with high pressures. In particular the pumping chamber and the riser pipe are adapted for high pressures, such as in the range from about 10 bar to about 100 bar.

The interior volume of the pumping chamber is changeable by means of relative motion of the pumping chamber to the riser pipe. This means that either the pumping chamber is moveable and the riser pipe is fixed, or the pumping chamber is fixed and the riser pipe is moveable, or both pumping chamber and riser pipe are moveable. A gap is present between an outside of said riser pipe and an inside of said pumping chamber, and a seal bridges said gap in order to minimize pressure loss when a pressure is generated inside said pumping chamber. Said seal must also be suitable to be used with high pressures, such as in the range from about 10 bar to about 100 bar.

According to the invention, said seal is fixed to said outside of said riser pipe. Accordingly, said seal is moveable—together with the riser pipe to which it is fixed—with respect to said inside of said pumping chamber. This relative motion of seal and pumping chamber is present when the pumping chamber is moveable and the riser pipe is fixed, as well as vice-versa.

This solution provided by the present invention results in a transport of abrasive particles, stemming from friction between riser pipe and pumping chamber, not into liquid F, but into the opposite direction, during the high pressure emission phase. Therefore, the liquid is not contaminated by abrasive particles, which is a significant improvement with respect to the solutions known up to date in the field of inhalation devices.

Furthermore, the outside wall quality of riser pipe must not be particularly high, since neither it moves along the seal, thus not resulting in any abrasion caused by such movement, nor any complex measures must be taken in order to make gap as small as possible, since also larger gaps can securely be bridged by an accordingly selected and arranged seal.

Another advantage over a solution known in the art is that the assembly of said seal becomes easier since the outside of the riser pipe is much better accessible than the inside of the pumping chamber.

Further, the construction becomes more simple. In a solution known in the art, due to the poor accessibility of the inside of the pumping chamber, a recess at the end of the hole provided to receive the pipe, followed by a lid, served as a workaround for forming a groove for the seal instead of directly manufacturing the groove in the wall of the pumping chamber. The present solution does not need such a workaround, and in particular, no such lid.

In a further aspect of the invention, an inhalation device for medically active liquids for generation of an aerosol comprises a housing, an impingement-type nozzle (6) for generating the nebulised aerosol by collision of at least two liquid jets, the nozzle (6) being firmly affixed to the user-facing side of the housing (1) such as to be immobile relative to the housing (1), inside the housing the inhalation device comprises a reservoir for storing a liquid, a pumping device with a pumping chamber for generation of a pressure inside said pumping chamber which is moveable relative to the housing or to the nozzle, wherein the pumping chamber is fluidically connected with the reservoir, a riser pipe which can be received with at least one reservoir-facing, interior end in said pumping chamber, and said nozzle which is connected liquid-tight to an exterior end of the riser pipe that is immobile and firmly attached to the housing or to the nozzle, wherein the interior volume of the pumping chamber is changeable by means of relative motion of the pumping chamber to the riser pipe (see above). According to the invention, a gap is present between an outside of said riser pipe and an inside of said pumping chamber, the gap being bridged by a seal for minimizing pressure loss when a pressure is generated inside said pumping chamber.

This aspect of the invention provides an improvement to the inhalation device disclosed in patent application EP17168869.0. By, according to the invention, allowing a gap between said surfaces and placing a seal in said gap, the surface smoothness of at least one of said surfaces, i.e. the outer surface of the riser pipe or the inner surface of the pumping chamber, does not necessarily require a very high quality.

In one of the preferred embodiments, the surface to which the seal is attached to is of a lower surface quality (higher roughness, less resistance to wear) than the adjacent surface, since only the surface along which the seal slides will contribute to a generation of undesired particles. The surface to which the seal is attached to is neither worn by the seal because it is immobile with respect to this surface, nor by the adjacent surface due to the gap. Thus, a high surface quality of the adjacent surface is sufficient.

Alternatively, and according to another preferred embodiment, the quality of the inner surface of the pumping chamber is essentially the same as the quality of the outer surface of the riser pipe.

According to a preferred aspect of the inhalation device, said seal is fixed to said outside of said riser pipe and moveable with respect to said inside of said pumping chamber. It is clear that said relative motion between seal and pumping chamber is not restricted to one of the aforementioned cases; rather, relative motion is possible both when the riser pipe or the pumping chamber are immobile with respect to the housing.

According to a preferred aspect of the aforementioned embodiment, said outside of said riser pipe exhibits a higher surface roughness than said inside of said pumping chamber. In other words, in the aforementioned situation, the surface quality of the outside of the riser pipe can be lower than the one of the inside of the pumping chamber. With respect to the pumping chamber, it is clear that herein as well as throughout the document, not its entire inside surface is meant, but in particular that region of the surface along which the seal slides upon pumping action. On the other hand, the outside of the riser pipe can have a low surface quality along its length (if no other restrictions exist that require otherwise, but which are not connected to the underlying problem of the present invention).

According to a further embodiment, said riser pipe exhibits a constricted region or an expanded region in order to accommodate or support said seal.

For example, a circumferential groove, or two circumferential ridges or shoulders can be used to fix the seal along the longitudinal axis of the outside of the riser pipe; the seal then sits in said groove or between said ridges or shoulders, respectively. It is clear that the depth of said groove or height of said ridges or shoulders must not exceed the thickness of said seal, but should amount to 10 to 90 percent, and preferably, to 20 to 50 percent, of the seal thickness (the thickness is measured perpendicular to the longitudinal axis of the riser pipe).

According to another embodiment, said seal is being fixed to said inside of said pumping chamber and moveable with respect to said outside of said riser pipe. In other words, the seal can slide along the outside surface of the riser pipe.

Preferably, said riser pipe exhibits a lower surface roughness than said inside of said pumping chamber. Since the seal does slide along the riser pipe, the latter can contribute to the generation of particles; hence, a high surface quality is preferred. On the other hand, the surface quality of the pumping chamber can be lower, since it is not exposed to any physically touching relative motion (friction).

Particularly preferred, said inside of said pumping chamber exhibits a recess or a rim. Thus, the aforementioned features (grooves, ridges, shoulders) can as well be used for fixing the seal to the inside of said pumping chamber.

It is clear that the seal can also be fixed by tension of its elastic material, by gluing, or by means of form-locking features (e.g. radially extending pins that fit into accordingly places boreholes of riser pipe or pumping chamber).

According to a preferred embodiment, the seal is an O-ring (round cross section) which is arranged in a groove of the outside of the riser pipe. The groove serves for precisely defining the position of the seal along the longitudinal axis of the riser pipe. If properly chosen, no additional fixation measures (like glue or clamping) are necessary. Preferably, the degree of tension is adapted to the requirements of the pumping chamber.

The seal can have also the shape of a flat ring (rectangular cross section). Such a seal can provide a larger contact area to both the part to which it is fixed, and the part along which it moves.

Another advantageous shape of a seal is a so called piston ring. Such a ring consists of a precisely manufactured ring which has a certain amount of elasticity, and a slit. By widening the seal, it can be pushed along the outside of the riser pipe until it reaches its seat (e.g. a groove). When the riser pipe, together with the seal, is then pushed into the opening of the pumping chamber, and due to said slit, the ring can be compressed until its outsides lie flat against the inner wall of the pumping chamber. One advantage is that the seal can be of a smaller volume, thus requiring a smaller seat. Further, in certain situations, it can be advantageous if the seal is made from metal, resulting in a particularly low abrasion rate.

The seal can have also the shape of a tube. Such a shape provides a particularly long contact area, improving the sealing effect, but also possibly increasing friction. Thus, Polytetrafluoroethylene is an example of a preferred material since it provides a very low friction coefficient with respect to both metal and plastics.

In a further embodiment the seal comprises a plurality of rings or a notched seal. In a particular embodiment, the seal has a plurality of contact planes with the pumping chamber. This arrangement shows a reduced leak rate if a dynamic pressure increase occurs as the different planes receive a different pressure load. This ultimate results in an improved holding time of the device.

In a further preferred embodiment, the seal comprises a tip in the crossection which forms the sealing plane in contact with the pumping chamber. This seal arrangement shows the highest surface pressure on the inner wall of the pumping chamber.

Besides an elastic material, said seal can be made of a material providing a particularly low friction, such as (but not limited to) aforementioned Polytetrafluoroethylene (PTFE). Also, metals or alloys are materials which can be used for a suitable seal; in particular, a piston ring like seal can be made of such a material.

It is of course possible to use compounds or composites for the seal, such as a metal body covered by PTFE, or a plastic ring on an elastic tube.

According to a further embodiment, the same comprises at least two of said seals are being arranged serially along the longitudinal axis of the riser pipe or of the respective opening within the pumping chamber, respectively. These seals can be of the same type and/or shape and/or material. Alternatively, two or more seals of differing type, shape and/or material may be used, depending on the requirements of the respective construction. A plurality of seals may provide a better seal effect than one single seal. This is particularly true for piston ring type seals.

According to a further embodiment, if more than one seal exists in the inhalation device, at least two of said seals, preferably being arranged serially, are sufficiently spaced apart such as to prevent a tilting of the riser pipe in the pumping chamber. In this context, tilting of the riser pipe should be understood as referring to the orientation of the riser pipe and the pumping chamber relative to each other, regardless of which part is moveable and which part is immobile. In other words, the seals are spaced apart to prevent non-parallel relative movement between the riser pipe and the pumping chamber. Thus, the mechanical functioning of the device is further improved.

DESCRIPTION OF FIGURES

In FIGS. 1 to 4, an exemplary inhalation device for medically active liquids as known from co-pending patent application EP17168869.0 is depicted schematically and not-to-scale. FIG. 1 shows the situation prior to first use.

Figure 1:
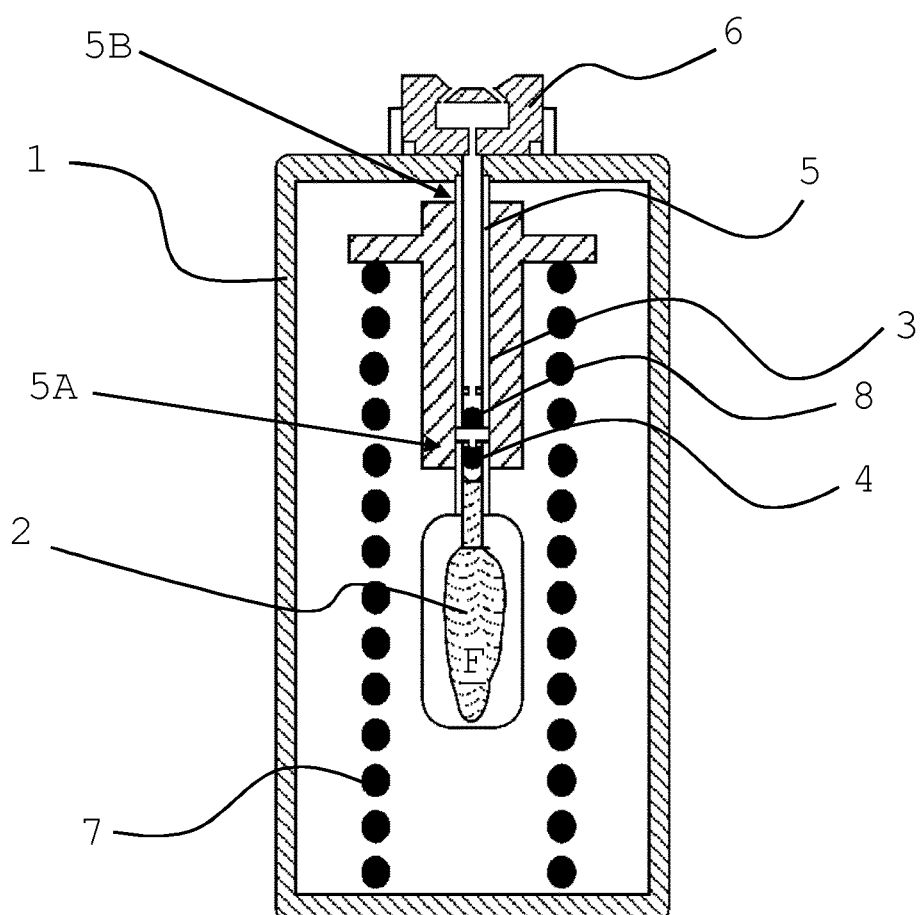
FIG. 1 shows schematically a known nebulizer for medically active liquids prior to its first use.
Figure 2:
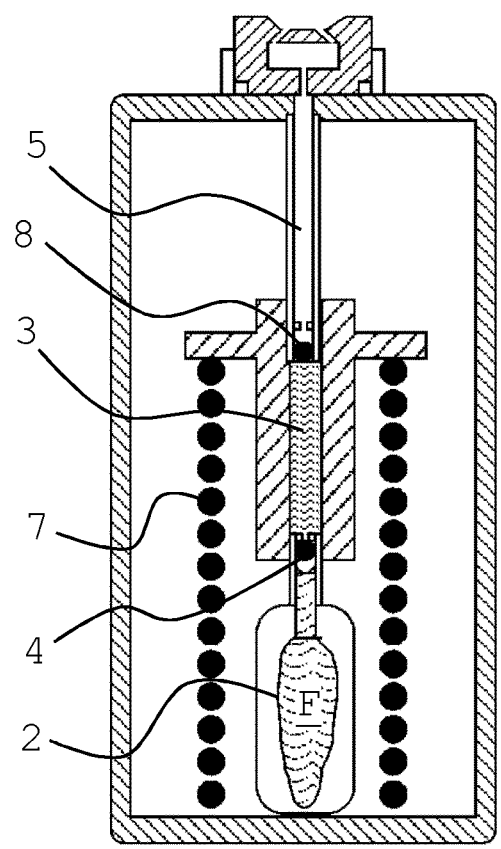
FIG. 2 shows the embodiment of FIG. 1 before initially filling the pumping chamber.
Figure 3:
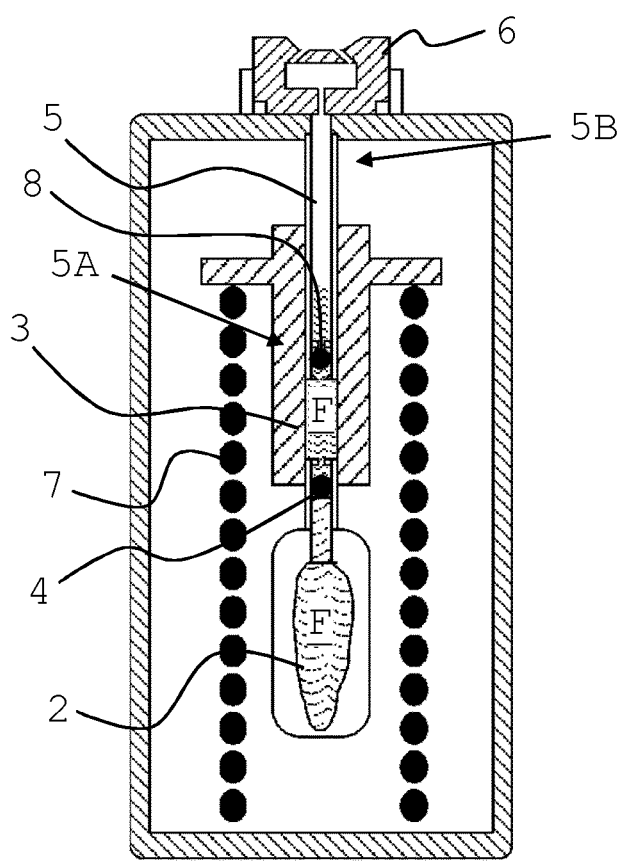
FIG. 3 shows the situation during the first activation.
Figure 4:
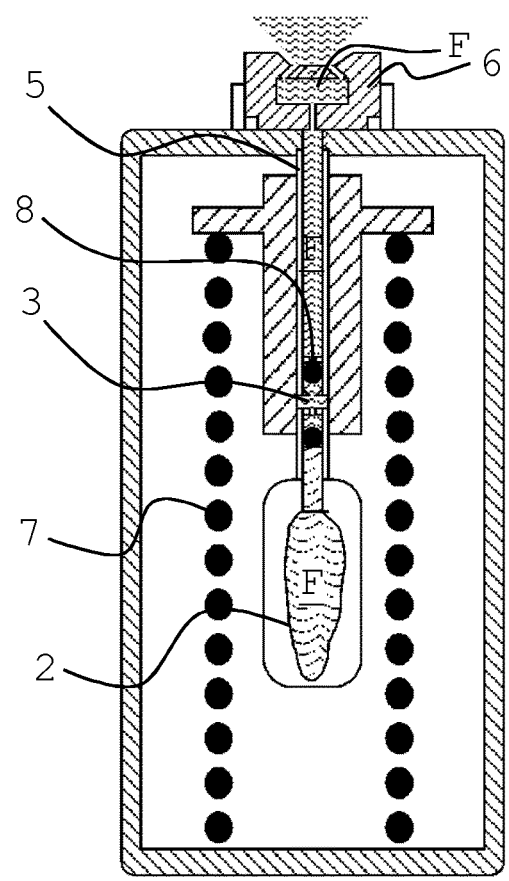
FIG. 4 shows the situation at the end of the first activation.
Figure 5:
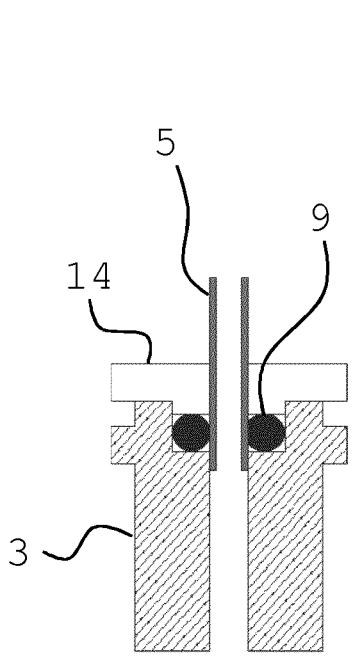
FIG. 5 shows an embodiment of the inhalation device with a seal being fixed to the pumping chamber.
Figure 6:
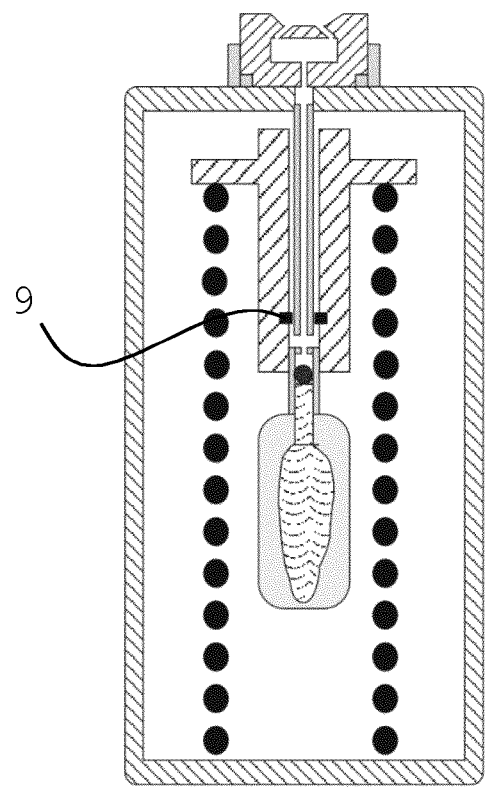
FIG. 6 shows a detail of another embodiment of an inhalation device with a seal being fixed to the pumping chamber.
Figure 7:
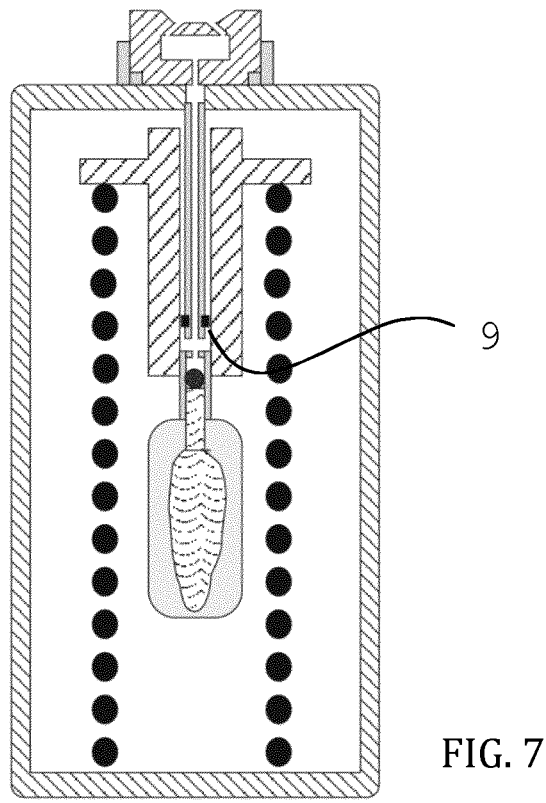
FIG. 7 shows an embodiment of the inhalation device with a seal being fixed to the riser pipe.

The inhalation device comprises a housing 1, which is preferably shaped and dimensioned such that it can be held with one hand and can be operated by one finger, e.g. the thumb (not shown). A reservoir 2 for storage of a medically active liquid F is located inside the housing 1. The depicted reservoir 2 is designed to be collapsible; that means that during proceeding emptying, the elastic or at least limp walls buckle, so that the underpressure which is necessary for extraction of a certain amount of liquid is not, or almost not, increased. A similar effect can be achieved when a rigid container has a moveable bottom by means of which the interior volume of the reservoir can also be successively be reduced (not shown).

Further, the inhalation device comprises a pumping device with a pumping chamber 3 within the housing 1 for generation of the desired pressure which is necessary for emitting liquid F and nebulizing the same. The pumping device can also comprise additional, not depicted components (push button, locking device, etc.).

Pumping chamber 3 is fluidically connected with reservoir 2 by means of an inlet check valve 4. Check valve 4 serves for allowing inflow of liquid F into the pumping chamber 3, and blocks a back flow of liquid F into reservoir 2 upon release of the not-depicted locking mechanism.

As a means for the storage of potential energy 7, a spring is provided which is coupled with one (upwards directed) end to the pumping chamber 3 and which is supported at housing 1 (lower part of the figure).

The inhalation device further comprises a riser pipe 5 with at least one reservoir-facing, interior end 5A which can be received in said pumping chamber 3. In other words, riser pipe 5 can at least partially be pushed into pumping chamber 3, resulting in a decrease of the interior volume of pumping chamber 3. The term “interior volume” describes that volume which extends from the reservoir-facing inlet of the pumping chamber 3 to the place where the interior end 5A of the riser pipe 5 is located. In the depicted situation, riser pipe 5 is almost entirely contained in the pumping chamber 3. As a result, the interior volume, situated between check valve 4 and the interior end 5A of riser pipe 5, is at a minimum.

Preferably, in the section which serves for the reception of the riser pipe, pumping chamber 3 has section with an circular inner cross section that corresponds to the (then also) circular outside cross section of the according riser pipe section. Of course, other cross section shapes are possible as well.

In order to minimize leakage and prevent liquid F from leaving pumping chamber 3 in an undesired way, according to one solution known in the art, the surface roughness of both the outside of riser pipe 5 as well as the respective inside surface section of pumping chamber 3 is very low, so that both surfaces virtually touch each other.

According to the depicted embodiment, check valve 4 is arranged between reservoir 2 and inlet of pumping chamber 3.

Finally, the inhalation device comprises a nozzle 6 which is connected liquid-tight to an exterior end 5B of riser pipe 5. Nozzle 6 can be any known nozzle which is suitable for nebulizing/atomizing liquid. The nozzle 6 which is depicted as an example uses the principle of nebulization by means of two colliding liquid jets. Preferably, the cross sections of the liquid-containing channels are relatively small, and typically, in the region of microns.

Also depicted is an optional outlet valve 8 inside riser pipe 5 for avoiding back flow of liquid or air into the exterior end 5B of the same from the outside. Outlet valve 8 is arranged in the interior end 5A of riser pipe 5. Liquid F can pass outlet valve 8 in direction of nozzle 6, but outlet valve 8 blocks any undesired back flow in the opposite direction.

As can be seen in FIG. 1, in the depicted example, riser pipe 5 is designed immobile and firmly attached to housing 1, indicated by the connection in the region of exterior end 5B with housing 1. Riser pipe 5 is also firmly attached to nozzle 6, which in turn is attached to housing 1 as well. On contrary, pumping chamber 3 is designed to be moveable with respect to housing 1 and nozzle 6. The benefits of this design have already been explained; reference is made to the respective sections above. It is noted that the invention can be used as well in the case of an immobile pumping chamber and a moveable piston.

FIG. 2 shows the embodiment of FIG. 1 when initially filling pumping chamber 3. Pumping chamber 3 is pulled down, loading the means for the storage of potential energy 7. Outlet valve 8 is closed due to underpressure inside pumping chamber 3, and check valve 4 is open to reservoir 2. In the following, this situation is also referred to as the “low pressure phase”. Increasingly collapsing walls of reservoir 2 allow its inside pressure remain nearly constant, while pressure inside pumping chamber 3 drops because of the downwards motion pulling pumping chamber 3 off riser pipe 5, increasing the interior volume of pumping chamber 3.

As a result, interior volume of pumping chamber 3 fills with liquid F from the reservoir.

In FIG. 3, the situation during the first activation of the inhalation device is shown. Means for the storage of potential energy 7 has been released from the loaded position as shown in FIG. 2. It pushes the pumping device comprising pumping chamber 3 onto riser pipe 5, the interior end 5A of which coming closer to check valve 4 now being closed. As a result, the pressure inside pumping chamber 3 rises and keeps valve 4 being closed, but opens outlet valve 8. Liquid F rises inside riser pipe 5 towards its exterior end 5B and nozzle 6. This situation is also referred to as the “high pressure phase” or “emission phase”.

FIG. 4 shows the situation at the end of the first (or any subsequent) activation. Means for the storage of potential energy 7 is in its most relaxed end position (spring fully extended). Also, pumping chamber 3 has been pushed almost entirely onto riser pipe 5 such that the interior volume of pumping chamber 3 reaches its minimum. Most of liquid F previously contained inside pumping chamber 3 has passed outlet valve 8 into riser pipe 5. Liquid F already contained within riser pipe 5 has been pushed towards, and though, nozzle 6, where the desired nebulization takes place, producing a spray. This situation is also referred to as the “emission phase” which is also part of aforesaid “high pressure phase”.

In FIG. 5, a schematic detail of another inhalation device known in the art is depicted. This detail shows a riser pipe 5 which is partially inserted in a corresponding bore hole of a pumping chamber 3. A seal 9 is located at the top end of the pumping chamber inside a recess forming a shoulder, the recess being closed by a lid 14, thus forming a groove dimensioned to accommodate the seal. Thus, when moving riser pipe 5 with respect to pumping chamber 3, friction between seal 9 and riser pipe 5 occurs which can result in abrasion of particles (not shown). Further, the depicted construction makes use of a certain number of individual pieces and geometrical features, making it difficult to fabricate.

Looking at FIGS. 6 and 7, a situation comparable to the one shown in FIG. 4 is depicted, but with the spray being omitted, as well as already introduced reference numerals. However, in addition to the previous figures, a seal 9 is present which is placed at slightly different locations in FIG. 6 and FIG. 7, respectively. Note that, with regard to said location, the situation of the device shown in FIG. 5 is comparable to the situation of the device shown in FIG. 6, i.e. seal 9 is attached to pumping chamber 3 in both cases.

As can be seen more precisely in FIGS. 8 and 9 which show details of FIGS. 6 and 7, respectively, seal 9 is arranged in a gap 10 which is present between the outside of the riser pipe 5 and the inside of the pumping chamber 3.

Figure 8:
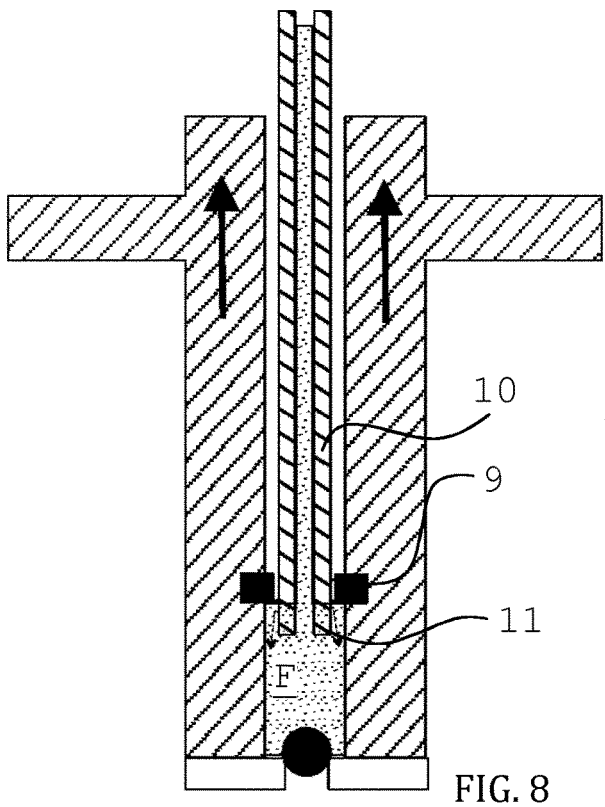
FIG. 8 shows a detail of FIG. 6.
Figure 10:
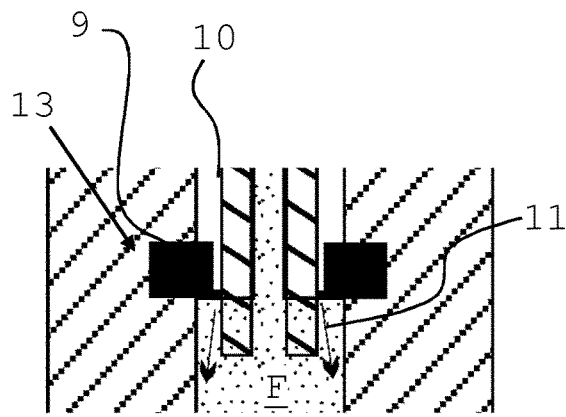
FIG. 10 shows a detail of FIG. 8.
Figure 9:
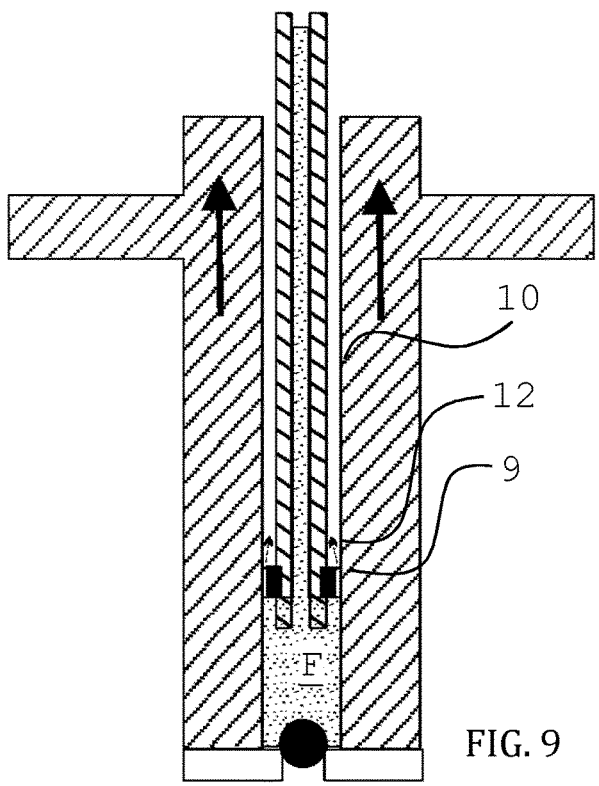
FIG. 9 shows a detail of FIG. 7.
Figure 11:
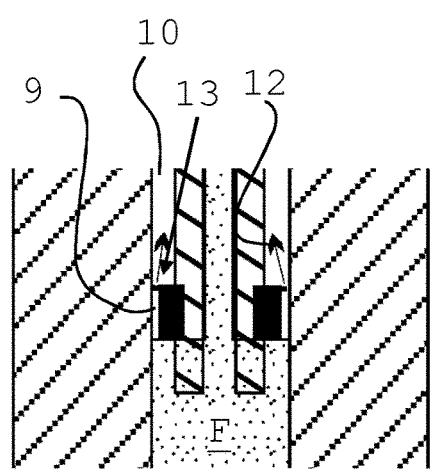
FIG. 11 shows a detail of FIG. 9.

While in the example of FIG. 10, showing a further detailed view of FIG. 8, seal 9 is fixed to the inside of pumping chamber 3, in the device as shown in FIG. 11, showing a further detailed view of FIG. 9, said seal 9 is fixed to the outside of riser pipe 5, and thus moveable with respect to inside of pumping chamber 3.

In the present examples, seal 9 is respectively arranged in a circumferential groove 13, which in FIG. 11 is arranged in the outside of riser pipe 5, whereas in FIG. 10, groove 13 is arranged in the inside wall of pumping chamber 3.

An additional advantage achieved with the embodiment of FIG. 9 and FIG. 11 wherein the seal 9 is fixed to the riser pipe 3 is that, during the depicted high pressure and emission phase, particles which may in some cases be formed from the seal 9 by abrasion or friction are not released into the liquid F, as in the case of the embodiments of FIG. 8 and FIG. 10, but into the opposite direction, as indicated by the arrows 11 and 12, respectively.

Hence, during said phase, liquid F is not contaminated by abrasive particles, which is a significant improvement with respect to the solutions known up to date in the field of inhalation devices.

Although a certain possibility exists that, during the subsequent low pressure phase which serves for refilling the pumping chamber 3, particles might be drawn back into the pumping chamber through region of the seal 9, the extent of contamination by particles during this phase is significantly lower. Firstly, the significantly lower pressure itself leads to a smaller amount of particle laden liquid F which can pass seal 9 during movement. Secondly, since the pressure which is rather close to ambient pressure (in the low pressure phase, the maximum possible difference is 1 bar, compared to 200 bar and more during the high pressure phase), the mechanical load which leads to friction and thus abrasion is significantly lower as well. Hence, less particles are generated during the low pressure phase, and thus, less particles will be transported into the pumping chamber 3.

Furthermore, the outside wall quality of riser pipe does not have to be particularly high if the seal is fixed to the riser pipe as shown in FIG. 9 and FIG. 11. Neither moves the outside wall along the seal, thus not resulting in any abrasion caused by such movement, nor must any complex measures be taken in order to make gap 10 as small as possible, because also larger gaps can securely be bridged by an accordingly selected and positioned seal 9.

In fact, only that section of inside wall of pumping chamber 3 which comes into contact with seal 9 should be of a high quality (low surface roughness, high wear resistance). However, if pumping chamber 3 is fabricated e.g. by injection moulding or the like, only one high quality master must be provided which can then be used for fabrication of a large number of pumping chambers, all providing accordingly high quality inside wall sections. Thus, the solution according to the invention provides also a cost effective solution.

Figure 12:
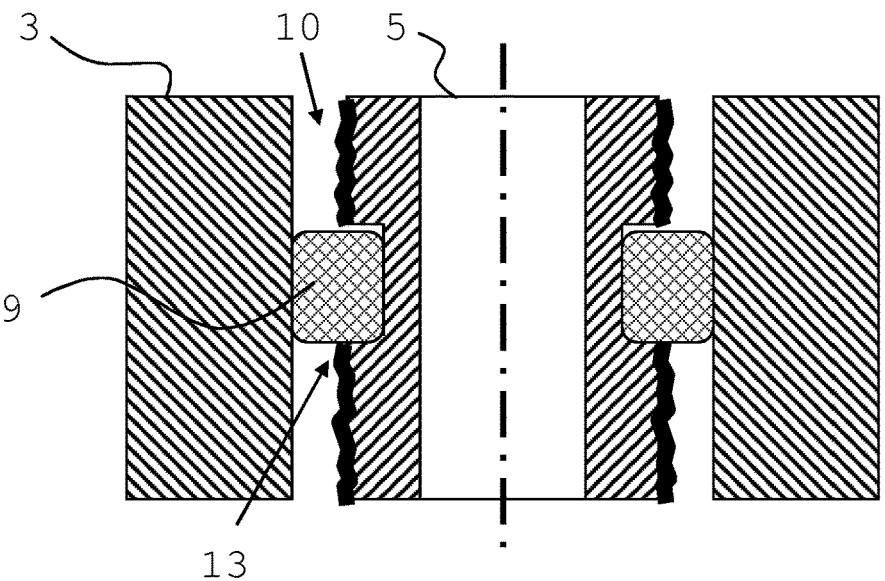
FIGS. 12-14 show schematic sectional views of different embodiments regarding the arrangement of a seal.

In FIG. 12, a schematic sectional view of the region with seal 9 is depicted. In this embodiment, seal 9 is located in a groove 13 which is arranged at the outside of riser pipe 5 (only a section thereof is shown). As can be seen, the surface quality of said outside can be rather low, since it does not come in physical contact with the inside wall of pumping chamber 3. Gap 10 is bridged by seal 9. Only the surface quality of the inside wall of pumping chamber should be high. The various surface qualities are indicated by a bumpy and a flat line in the drawing, respectively.

Figure 13:
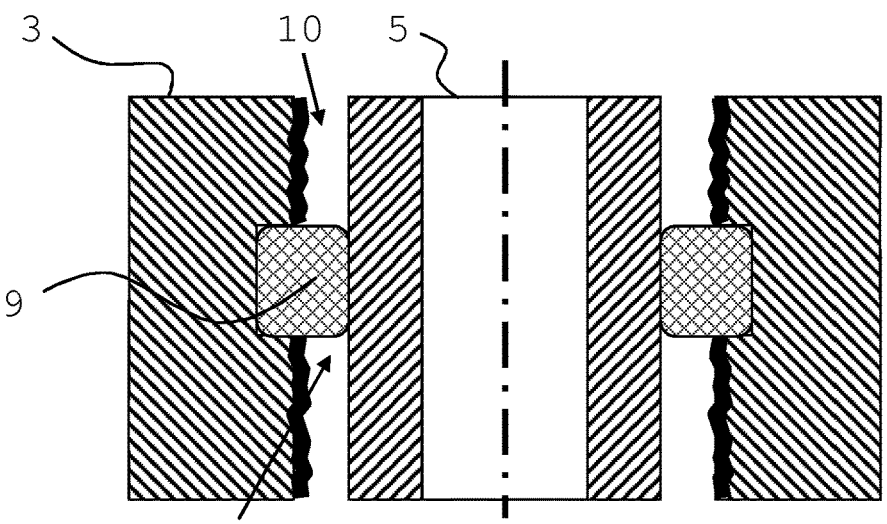

In FIG. 13, the situation is depicted with seal 9 being fixed to the pumping chamber 3. Again, a groove 13 holds seal 9 in place. Vice-versa to the previous embodiment, now, surface quality of riser pipe 5 should be high, whereas surface quality of pumping chamber 3 can be low.

Figure 14:
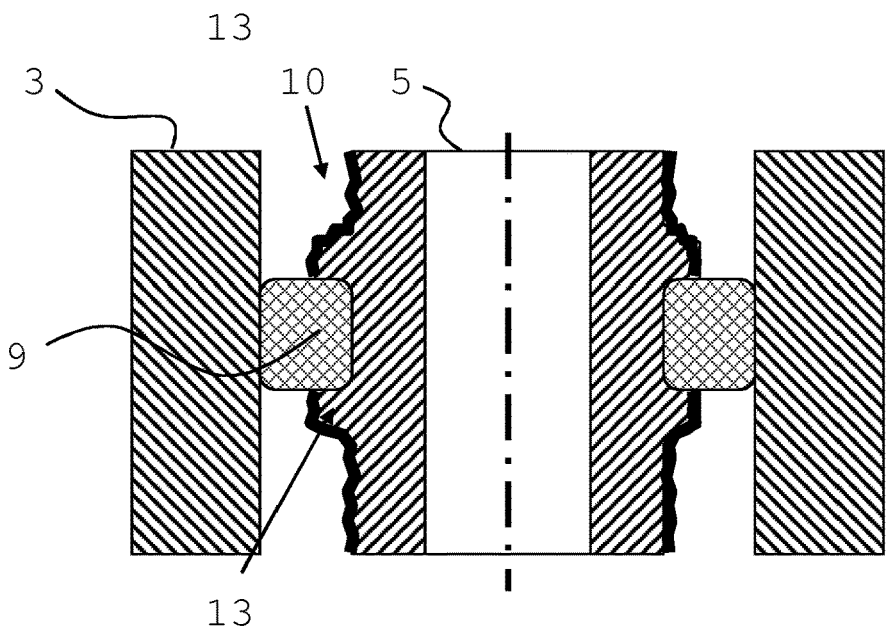

In FIG. 14, which shows a basic situation comparable to the one in FIG. 12, seal 9 rests against two shoulders which extend radially from the otherwise flat outside of riser pipe 5. The space between said shoulders is dimensioned so that seal 9 cannot slide along longitudinal axis of riser pipe 5 (dash-dotted vertical line), and again, surface quality of outside of riser pipe 5 can be low.

Figure 15:
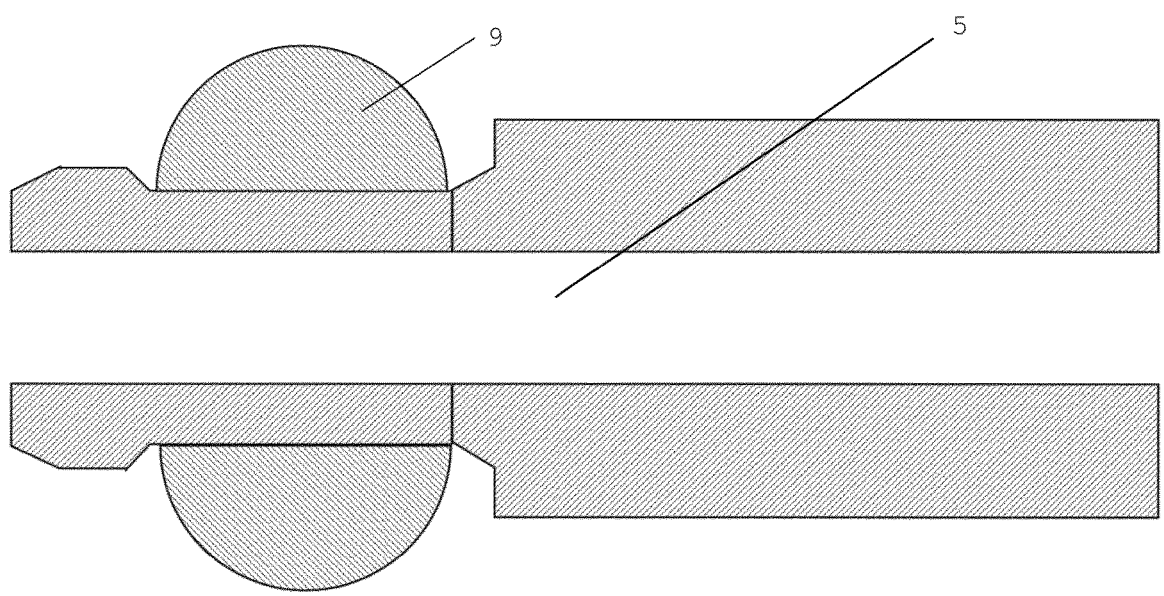
FIGS. 15-17 show schematic sectional views of different embodiments regarding the shape of a seal.

FIG. 15 shows a preferred seal arrangement in side view. In this case the seal is an o-ring with round cross section. The o-ring is in contact with the pumping chamber and can be arranged in a grove of the riser pipe.

Figure 16:
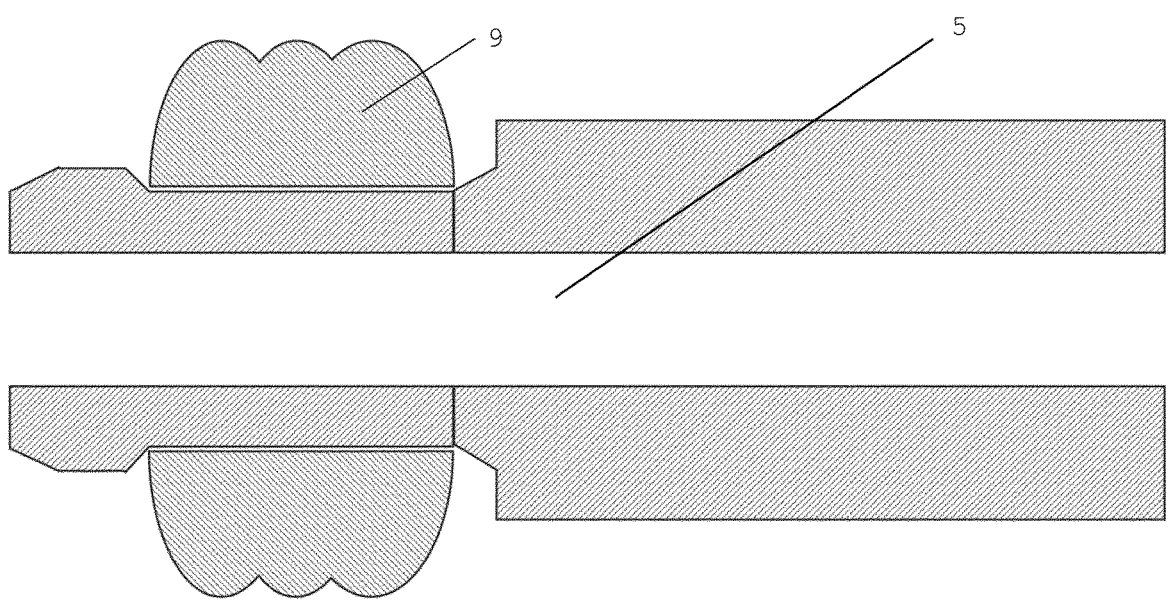

FIG. 16 shows an alternative seal arrangement comprosing a pluratity of sealing planes, either arranged due to a plurality of rings, or through the shape of the seal, e.g. by including one or more notches in the seal.

Figure 17:
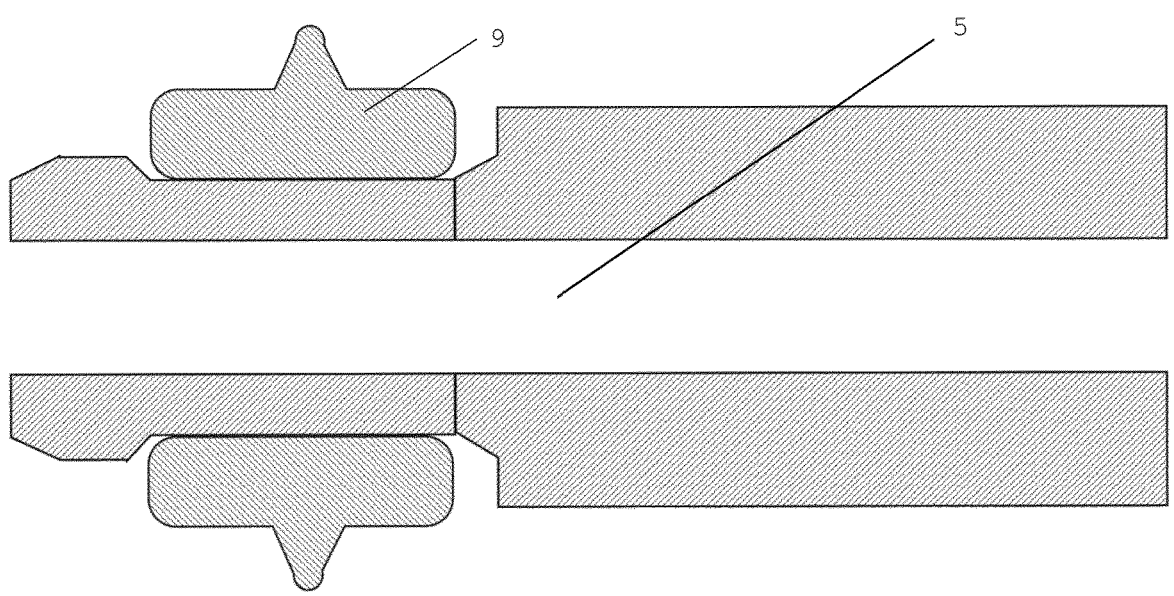

FIG. 17 shows a further alternative seal arrangement, showing a protruding tip from a broader base of the seal. This arrangement allows for high surface pressure to the inner wall of the pumping chamber.

LIST OF REFERENCES 1 housing
2 reservoir
3 pumping chamber
4 check valve
5 riser pipe
5A interior end
5B exterior end
6 nozzle
7 means for the storage of potential energy
8 outlet valve
9 seal
10 gap
11 arrow
12 arrow
13 groove
14 lid
F liquid

The invention claimed is:

1. An inhalation device for medically active liquids for generation of an aerosol, comprising:
a housing;
an impingement nozzle for generating the nebulised aerosol by collision of at least two liquid jets, the nozzle being firmly affixed to a user-facing side of the housing so as to be immobile relative to the housing;
inside the housing the inhalation device comprises:
a reservoir for storing a liquid;
a pumping device with:
a pumping chamber for generation of a pressure inside said pumping chamber which is moveable relative to the housing or to the nozzle, wherein the pumping chamber is fluidically connected with the reservoir;
a riser pipe which can be received with at least one reservoir-facing, interior end in said pumping chamber, and said nozzle which is connected liquid-tight to an exterior end of the riser pipe that is immobile and firmly attached to the housing or to the nozzle, wherein the interior volume of the pumping chamber is changeable by means of relative motion of the pumping chamber to the riser pipe, wherein the pumping chamber is pushed onto the immobile riser pipe to increase the pressure and press the medically active liquid out of the nozzle;

characterized in that a gap is present between an outside of said riser pipe and an inside of said pumping chamber, the gap being bridged by a seal for minimizing pressure loss when a pressure is generated inside said pumping chamber.

2. The inhalation device according to claim 1, wherein said seal is fixed to said outside of said riser pipe.

3. The inhalation device according to claim 2, wherein said outside of said riser pipe exhibits a higher surface roughness than said inside of said pumping chamber.

4. The inhalation device according to claim 3, wherein said riser pipe exhibits a constricted region or an expanded region.

5. The inhalation device according to claim 2, wherein said riser pipe exhibits a constricted region or an expanded region.

6. The inhalation device according to claim 1, wherein said seal is being fixed to said inside of said pumping chamber and moveable with respect to said outside of said riser pipe.

7. The inhalation device according to claim 6, wherein said outside of said riser pipe exhibits a lower surface roughness than said inside of said pumping chamber.

8. The inhalation device according to claim 7, wherein said inside of said pumping chamber exhibits a recess or a rim.

9. The inhalation device according to claim 6, wherein said inside of said pumping chamber exhibits a recess or a rim.

10. The inhalation device according to claim 1, wherein said seal is an O-ring, a flat ring, a piston ring, or a tube.

11. The inhalation device according to claim 1, wherein said seal is made of an elastomer, Polytetrafluoroethylene, or a metal.

12. The inhalation device according to claim 1, wherein the inhalation device comprises at least two of said seals, being arranged serially.

13. The inhalation device according to claim 12, wherein at least two of said seals are spaced apart so as to prevent a tilting of the riser pipe in the pumping chamber.

14. The inhalation device according to claim 1, wherein the generation of the aerosol occurs without a propellant.

* * * * *